United States Patent [19]
Edwards

[11] Patent Number: 4,943,274
[45] Date of Patent: Jul. 24, 1990

[54] APPARATUS FOR APPLYING EARLOBE MEDICATION

[76] Inventor: Judy S. Edwards, 114 W. 14th St., Irving, Tex. 75060

[21] Appl. No.: 349,320

[22] Filed: May 8, 1989

[51] Int. Cl.⁵ .............................................. A61M 35/00
[52] U.S. Cl. ......................................... 604/2; 604/290
[58] Field of Search ........................... 604/2, 289, 290; 128/330, 329 R

[56] References Cited

U.S. PATENT DOCUMENTS 1,899,492  2/1933  Beebe .
2,568,207  9/1951  Spicher .
3,500,829  3/1970  Abramowitz .
3,821,956  7/1974  Gordhamer .
4,067,341  1/1978  Ivey .

FOREIGN PATENT DOCUMENTS

87/06143 10/1987 World Int. Prop. O. .............. 604/2

Primary Examiner—John D. Yasko
Attorney, Agent, or Firm—Daniel V. Thompson

[57] ABSTRACT

Apparatus for insertion through an aperture in an earlobe includes structure for delivering medicament to the aperture. In one embodiment, a resilient reservoir for medicament is used to supply medicament through an apertured conduit. In another embodiment, a medicated string is pulled needle-and-thread fashion through the earlobe aperture and retained therein.

3 Claims, 1 Drawing Sheet

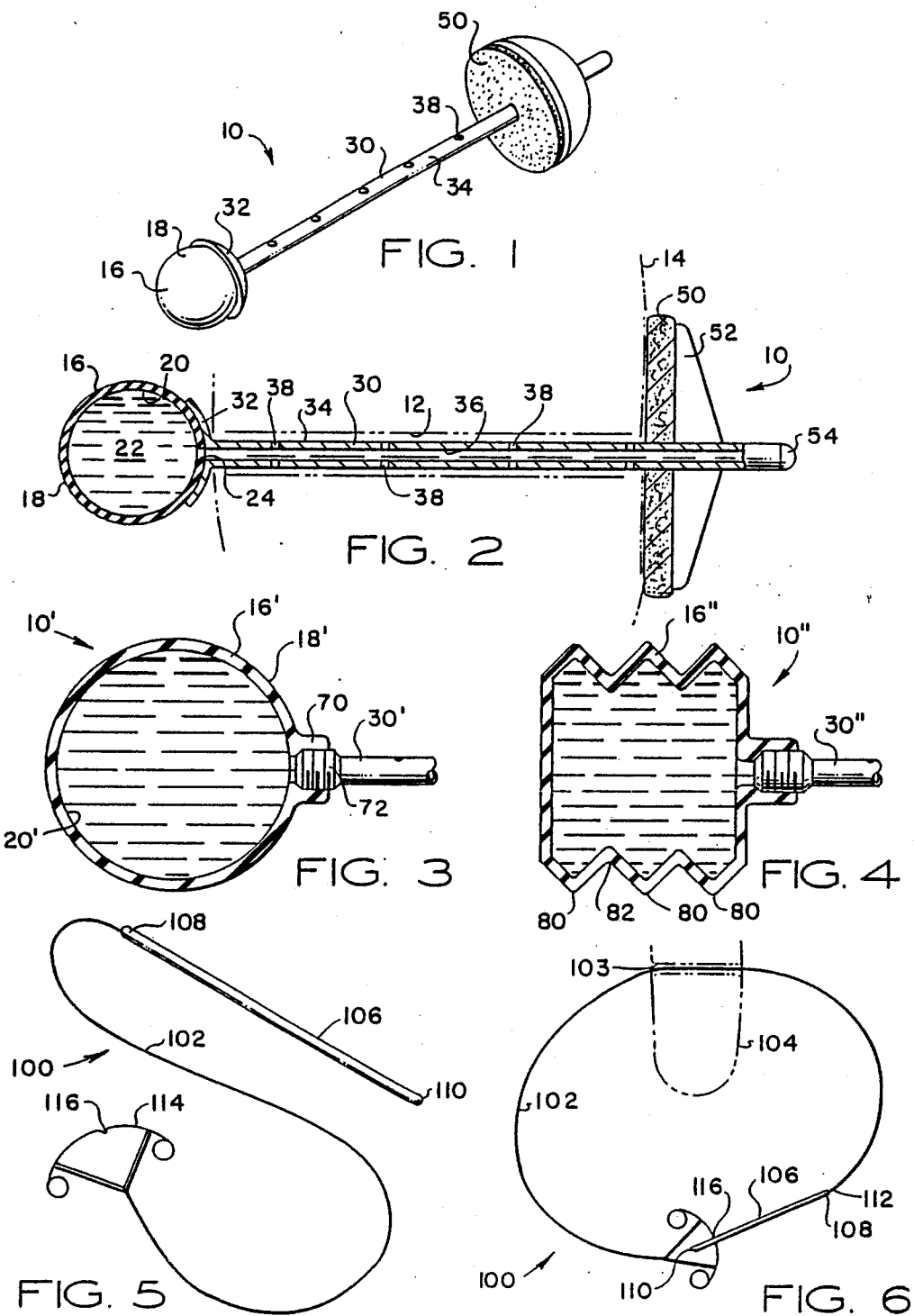

APPARATUS FOR APPLYING EARLOBE MEDICATION

TECHNICAL FIELD

This invention relates generally to apparatus for applying medicaments, and more particularly to apparatus for applying medicaments to apertures in earlobes.

BACKGROUND OF THE ART

Earrings have been worn for ornamentation since early times, and one popular means for attaching earrings has involved the piercing the earlobes to accommodate the earrings. In modern times, the most usual practice for forming the aperture has been to force a needle or the like through the earlobe, with a local anesthetic being used to reduce the pain accompanying the procedure. The aperture, being a wound in the earlobe, will in due course heal provided no infection occurs. It is also common to leave an object in the aperture during the healing process, so that the wound does not heal over and thereby close the aperture. Thus, it is conventional to position an earring in the aperture as soon as the lobe has been pierced, although in some cases wires or pieces of thread have been left in the aperture to prevent the aperture from closing during the healing of the wound. None of these prior art techniques have been effective in reducing the pain of the operation or avoiding the frequent infection which has accompanied the earlobe-piercing procedure.

Thus, there presently exists a need for apparatus which will conveniently and effectively deliver medicament to the aperture in an earlobe during the healing period following a piercing operation.

SUMMARY OF THE INVENTION

The present invention provides apparatus for supplying medicament to the interior and adjacent exterior areas of a newly pierced earlobe. In accordance with one aspect of the invention, a tube having radial apertures is inserted into the earlobe aperture, and a resilient medicament reservoir is attached to the tube. The interior of the reservoir communicates with the interior of the tube, such that pressure applied to the reservoir will cause medicament to be exuded through the apertures in the tube to the aperture in the earlobe. Alternate embodiments for the reservoir are provided, including a threaded spherical reservoir and a threaded, pleated bellows reservoir. In another aspect of the invention, a medicated felt pad is supplied for use in combination with an earring back. The felt pad supplies medicament to the inner earlobe surface adjacent the aperture. In yet another aspect of the invention, a medicated string is connected to an elongated cylindrical bar at one end and a retainer on the other end. The bar is passed through the aperture such that the medicated string is retained therein. The retainer and elongated bar are then connected to prevent loss of the apparatus.

BRIEF DESCRIPTION OF THE DRAWINGS

A more complete understanding of the invention and its advantages will be apparent from the Detailed Description taken in conjunction with the accompanying Drawings in which, FIG. 1 is a perspective view of a first embodiment of the invention;

FIG. 2 is a partially broken away side view of the embodiment of FIG. 1;

FIG. 3 is a partially broken away side view of a second embodiment of the invention;

FIG. 4 is a partially broken away side view of a third embodiment of the invention;

FIG. 5 is a schematic representation of yet another embodiment of the invention utilizing medicated string; and, FIG. 6 is a view similar to FIG. 5 showing the apparatus placed relative an earlobe aperture.

DETAILED DESCRIPTION OF THE PREFERRED EMBODIMENT

Referring initially to FIGS. 1 and 2, apparatus 10 is provided for insertion into an aperture 12 in an earlobe 14. Apparatus 10 includes a resilient housing 16, which may be formed of any of a number of suitable materials such as neoprene, polypropylene or polyethylene. Resilient housing 16 has exterior walls 18 and interior walls 20. Interior walls 20 define a reservoir for medicament 22, which can comprise any of numerous medicaments including antibiotic gel, petrolatum or aloe-based ointments. In the embodiment shown in FIGS. 1 and 2, exterior and interior walls 18 and 20, respectively, are spherical. Cylindrical walls 24 define an opening through exterior and interior walls 18 and 20, respectively.

A tubular conduit 30 is connected to and extends from reservoir 16. A semi-spherical, outwardly-concave collar 32 is connected to one end of conduit 30. Collar 32 has an inner curved surface having a contour that closely matches the curvature of exterior walls 18 of reservoir 16, such that collar 32 may be bonded to exterior wall 18 by any suitable adhesive technique. Conduit 30 has outer cylindrical longitudinal wall 34 and inner cylindrical longitudinal wall 36. Inner wall 36 at the end of conduit 30 surrounded by collar 32 communicates with cylindrical wall 24 which defines the opening to the interior of reservoir 16. Thus, inner cylindrical wall 36 communicates with the interior of reservoir 16. A plurality of radial cylindrical walls 38 form apertures between inner and outer longitudinal walls 36 and 34, respectively.

A felt pad 50 is soaked in medicament prior to utilization as a backing pad for retainer 52. Optionally, felt pad 50 can be permanently attached to retainer 52 or be packaged separately therefrom. In either situation, felt pad 50 may be supplied with medicament already applied, or can be supplied without medicament such that the user can apply the medicament of his/her choice. End 54 of conduit 30 is closed.

Referring now to FIG. 3, an alternate embodiment of apparatus 10' includes a reservoir 16' having spherical inner and outer walls 20' and 18', respectively. The semi-spherical collar 32 of FIGS. 1 and 2 has been eliminated in favor of a threaded connection between reservoir 16' and conduit 30'. The threaded connection includes a female threaded outlet 70 fixed to reservoir 16' and a male threaded end 72 of conduit 30'.

Referring now to FIG. 4, another alternate embodiment of apparatus 10" includes reservoir 16" having a threaded coupling between the reservoir and conduit 30". Reservoir 16", rather than being spherical, is of a pleated, bellows shape having large diameter pleats 80 and small diameter portions 82 between pleats 80. It will be understood that reservoir 16" has circular cross sections taken about the longitudinal axis of conduit 30" and is coaxial with conduit 30".

In operation, the apparatus of FIGS. 1-4 is inserted through an aperture in an earlobe immediately after a piercing procedure. At various times during the day, the user can give the reservoir 16 a slight squeeze to pressurize medicament 22 such that medicament is forced through conduit 30 and out the apertures formed by walls 38. Thus, medicament is applied to the interior of the aperture in the earlobe. Medicated felt pad 50 serves to medicate the interior side of the earlobe adjacent the aperture and additionally serves to receive excess medicament exuded from conduit 30.

Referring now to FIGS. 5 and 6, another embodiment of the invention includes apparatus 100 wherein a medicated string 102 is pulled needle-and-thread fashion through the aperture 103 of earlobe 104. Apparatus 100 includes an elongated cylindrical bar 106 sized for passage through the aperture 103 and having first end 108 and second end 110. String 102 is connected at a first end 112 to first end 108 of bar 106. String 102 is impregnated with any one of a number of medicaments such as those discussed above in connection with reservoir 16. A retainer 114 is connected to a second end 116 of string 102. Preferably, retainer 114 is a conventional spring-type retainer having an aperture 116 adapted to grip and retain bar 106, as shown in FIG. 6.

In operation, apparatus 100 is inserted through the earlobe aperture by inserting second end 110 into the earlobe and pushing bar 106 through the aperture Bar 106 is then pulled from the opposite side of earlobe 104 such that a portion of string 102 is located within the earlobe aperture Second end 110 is then inserted into aperture 116 of retainer 114 such that the apparatus is maintained in position. String 102 can be shifted within the earlobe aperture to expose different portions of the string to the earlobe aperture and thereby increase the beneficial effect thereof.

Whereas the present invention has been described with respect to specific embodiments thereof, it will be understood that various changes and modifications will be suggested to one skilled in the art, and it is intended to encompass such changes and modifications as fall within the scope of the appended claims.

I claim:

1. Apparatus for insertion through an aperture in an ear lobe, comprising:
    a resilient housing having exterior and interior walls, said interior walls defining a reservoir for medicament, and said housing further having an opening through said exterior and interior walls defining an outlet;
    a tubular conduit connected to and extending from said outlet in said housing, said conduit having inner and outer cylindrical longitudinal walls, with a plurality of radial cylindrical walls forming apertures between said inner and outer longitudinal walls;
    said housing having a spherical exterior wall; and
    said conduit having a semispherical collar attached to an end thereof and joined to a portion of said housing exterior wall.

2. Apparatus for insertion through an aperture in an ear lobe, comprising:
    a resilient housing having exterior and interior walls, said interior walls defining a reservoir for medicament, and said housing further having an opening through said exterior and interior walls defining an outlet;
    a tubular conduit connected to and extending from said outlet in said housing, said conduit having inner and outer cylindrical longitudinal walls, with a plurality of radial cylindrical walls forming apertures between said inner and outer longitudinal walls;
    retaining means for retaining said apparatus in the earlobe; and
    a medicated felt pad interposed between said housing and said retaining means.

3. Apparatus for insertion through an aperture in an earlobe, comprising:
    an elongated cylindrical bar sized for passage through the aperture and having first and second ends;
    a length of string connected at a first end to said first end of the bar, said length of string being impregnated with medicament; and,
    retaining means attached to a second end of said length of string for removable engagement with said second end of said bar.

* * * * *